US012631799B2

(12) United States Patent
Sun et al.

(10) Patent No.: US 12,631,799 B2
(45) Date of Patent: May 19, 2026

(54) OPTICAL CONSTRUCTION AND OPTICAL SYSTEM

(71) Applicant: 3M INNOVATIVE PROPERTIES COMPANY, St. Paul, MN (US)

(72) Inventors: Xiaoguang Sun, Woodbury, MN (US); Zhaohui Yang, North Oaks, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 728 days.

(21) Appl. No.: 17/919,352

(22) PCT Filed: Mar. 17, 2021

(86) PCT No.: PCT/IB2021/052220
§ 371 (c)(1),
(2) Date: Oct. 17, 2022

(87) PCT Pub. No.: WO2021/214567
PCT Pub. Date: Oct. 28, 2021

(65) Prior Publication Data
US 2023/0161088 A1      May 25, 2023

Related U.S. Application Data

(60) Provisional application No. 62/704,087, filed on Apr. 21, 2020.

(51) Int. Cl.
G02B 3/00        (2006.01)
A61B 5/1172      (2016.01)
(Continued)

(52) U.S. Cl.
CPC .......... G02B 3/0056 (2013.01); A61B 5/1172 (2013.01); B32B 3/18 (2013.01);
(Continued)

(58) Field of Classification Search
CPC ...... G02B 3/0056; G02B 3/006; G02B 5/208; G02B 5/22; G02B 3/0006; G06V 40/1318;
(Continued)

(56) References Cited

U.S. PATENT DOCUMENTS 6,076,932 A       6/2000  Uchida et al.
9,457,544 B1 *   10/2016  Menon ................... B32B 17/06
(Continued)

FOREIGN PATENT DOCUMENTS

JP              2004333528 A      11/2004

OTHER PUBLICATIONS

JP 2004-333528 A, English language machine translation, generated Jul. 24, 2025 (Year: 2004).*
(Continued)

*Primary Examiner* — Stephone B Allen
*Assistant Examiner* — Adam W Booher
(74) *Attorney, Agent, or Firm* — Jonathan L. Tolstedt

(57) ABSTRACT

An optical construction includes a lens film and a mask layer. The lens film includes an outermost structured first major surface and an opposing outermost substantially planar second major surface. The first major surface includes a plurality of microlenses arranged along orthogonal first and second directions. The mask layer is disposed on the second major surface of the lens film and includes a first layer including a first metal, a second layer including a second metal and a third layer disposed between the first and second layers. For substantially normally incident light, each of the first and second layers has an optical reflectance of greater than about 5%, the third layer has an optical transmittance of greater than about 70%, and the mask layer has an optical
(Continued)

reflectance of less than about 20%. The mask layer defines a plurality of through openings aligned to the microlenses in a one-to-one correspondence.

10 Claims, 4 Drawing Sheets

(51) Int. Cl.

| | |
|---|---|
| *B32B 3/18* | (2006.01) |
| *B32B 7/12* | (2006.01) |
| *G02B 5/20* | (2006.01) |
| *G06V 40/13* | (2022.01) |

(52) U.S. Cl.
CPC ................ *B32B 7/12* (2013.01); *G02B 5/208* (2013.01); *G06V 40/1318* (2022.01); *B32B 2255/20* (2013.01); *B32B 2255/205* (2013.01); *B32B 2255/28* (2013.01); *B32B 2457/20* (2013.01)

(58) Field of Classification Search
CPC ......... A61B 5/1172; B32B 3/18; B32B 3/266; B32B 7/12; B32B 2255/20; B32B 2255/205; B32B 2255/28; B32B 2457/20
See application file for complete search history.

(56) References Cited

U.S. PATENT DOCUMENTS

| | | | |
|---|---|---|---|
| 10,360,432 | B1 | 7/2019 | He et al. |
| 2010/0067757 | A1 | 3/2010 | Arai et al. |
| 2011/0080824 | A1* | 4/2011 | Ito ............................ B32B 7/12 369/283 |
| 2019/0147214 | A1 | 5/2019 | Lee et al. |

OTHER PUBLICATIONS

International Search Report for PCT Application No. PCT/IB2021/052220, mailed on Jun. 8, 2021, 4 pages.

* cited by examiner

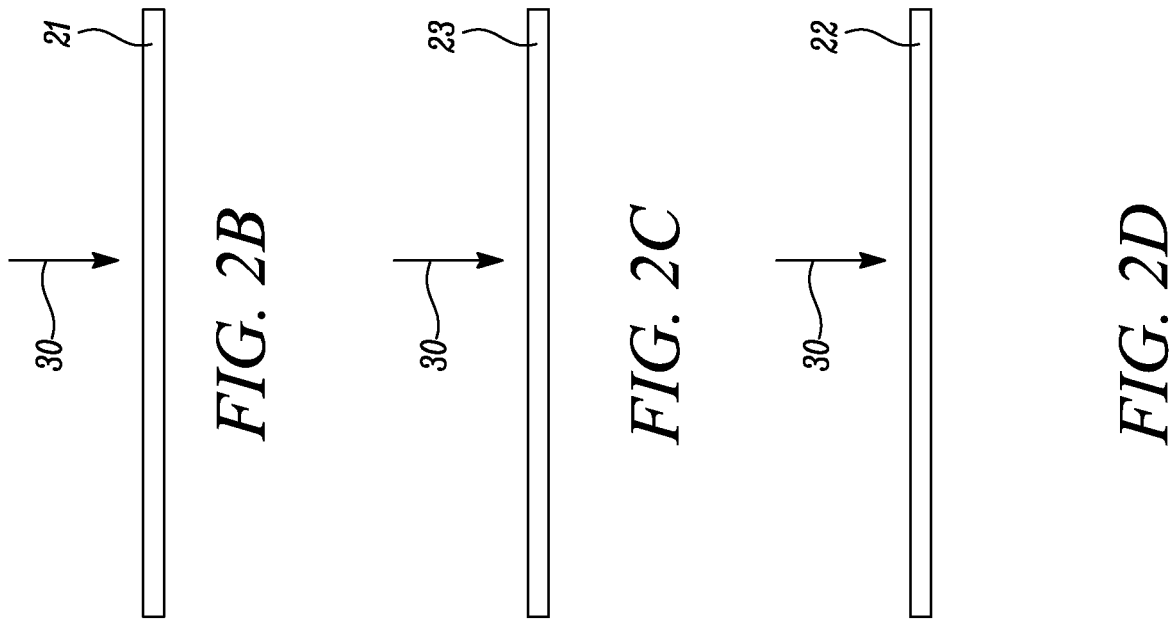
*FIG. 2B*
*FIG. 2C*
*FIG. 2D*
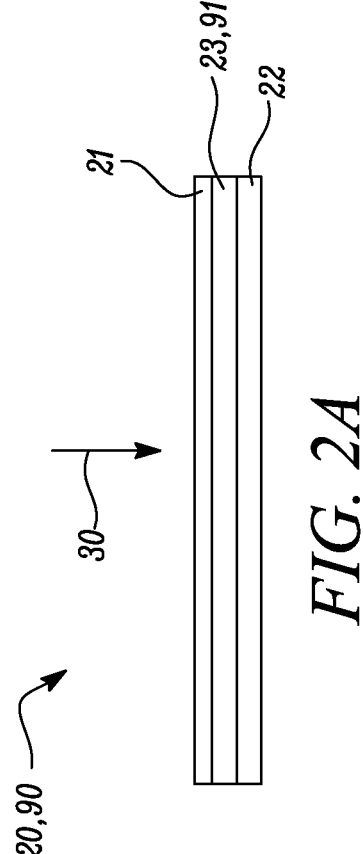
*FIG. 2A*

OPTICAL CONSTRUCTION AND OPTICAL SYSTEM

CROSS REFERENCE TO RELATED APPLICATIONS

This application is a national stage filing under 35 U.S.C. 371 of PCT/IB2021/052220 filed Mar. 17, 2021, which claims the benefit of U.S. Application No. 62/704,087, filed Apr. 21, 2020, the disclosures of which are incorporated by reference in their entireties herein.

TECHNICAL FIELD

The present disclosure relates generally to an optical construction and an optical system, and in particular, to an optical construction and an optical system for a display.

BACKGROUND

Devices, such as cell phones and tablets, can be equipped with biometric authentication features, such as fingerprint sensors. In some cases, the fingerprint sensors are incorporated under a display of the devices, and are referred to as under-the-display fingerprint sensors. The under-the-display fingerprint sensors turn a defined area of the display into a fingerprint sensor, thereby eliminating the need for a separate physical fingerprint sensor.

SUMMARY

In a first aspect, the present disclosure provides an optical construction. The optical construction includes a lens film including an outermost structured first major surface and an opposing outermost substantially planar second major surface. The structured first major surface includes a plurality of microlenses arranged along orthogonal first and second directions. The optical construction further includes a multilayer optically opaque mask layer disposed on the second major surface of the lens film opposite the structured first major surface. The multilayer optically opaque mask layer includes a first layer including a first metal and a second layer including a second metal. The multilayer optically opaque mask layer further includes a third layer disposed between the first and second layers. Each of the first, second and third layers has an average thickness less than about 200 nanometers (nm). The first layer is disposed between the second major surface of the lens film and the third layer, such that for substantially normally incident light and for at least one wavelength in a visible wavelength range extending from about 400 nm to about 600 nm, each of the first and second layers has an optical reflectance of greater than about 5%, the third layer has an optical transmittance of greater than about 70%, and the mask layer has an optical reflectance of less than about 20%. The mask layer defines a plurality of through openings therein extending through at least the first, second and third layers and arranged along the first and second directions. The through openings are aligned to the microlenses in a one-to-one correspondence.

In a second aspect, the present disclosure provides an optical system including a display including a plurality of light emitting pixels arranged along the first and second directions. The optical system further includes an optical sensor disposed proximate the display. The optical system further includes the optical construction of the first aspect disposed between the display and the optical sensor.

In a third aspect, the present disclosure provides an optical construction for absorbing visible light and transmitting infrared light. The optical construction includes a plurality of microlenses disposed on a substantially light absorbing optical cavity system and arranged along orthogonal first and second directions. The optical cavity system includes opposing first and second reflectors defining an optical cavity therebetween. The optical cavity has a length less than 200 nm, such that for substantially normally incident light and a visible wavelength range extending from about 400 nm to about 600 nm, for at least one wavelength in the visible wavelength range, the optical cavity system reflects less than about 20% of the incident light, and transmits less than 2% of the incident light and for at least one wavelength in the visible wavelength range, the optical construction transmits at least 10% of the incident light.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

FIG. 2A is a schematic view of a multilayer optically opaque mask layer according to one embodiment of the present disclosure;

FIG. 2B is a schematic view of a first layer of the multilayer optically opaque mask layer according to one embodiment of the present disclosure;

FIG. 2C is a schematic view of a second layer of the multilayer optically opaque mask layer according to one embodiment of the present disclosure;

FIG. 2D is a schematic view of a third layer of the multilayer optically opaque mask layer according to one embodiment of the present disclosure;

DETAILED DESCRIPTION

Figure 1:
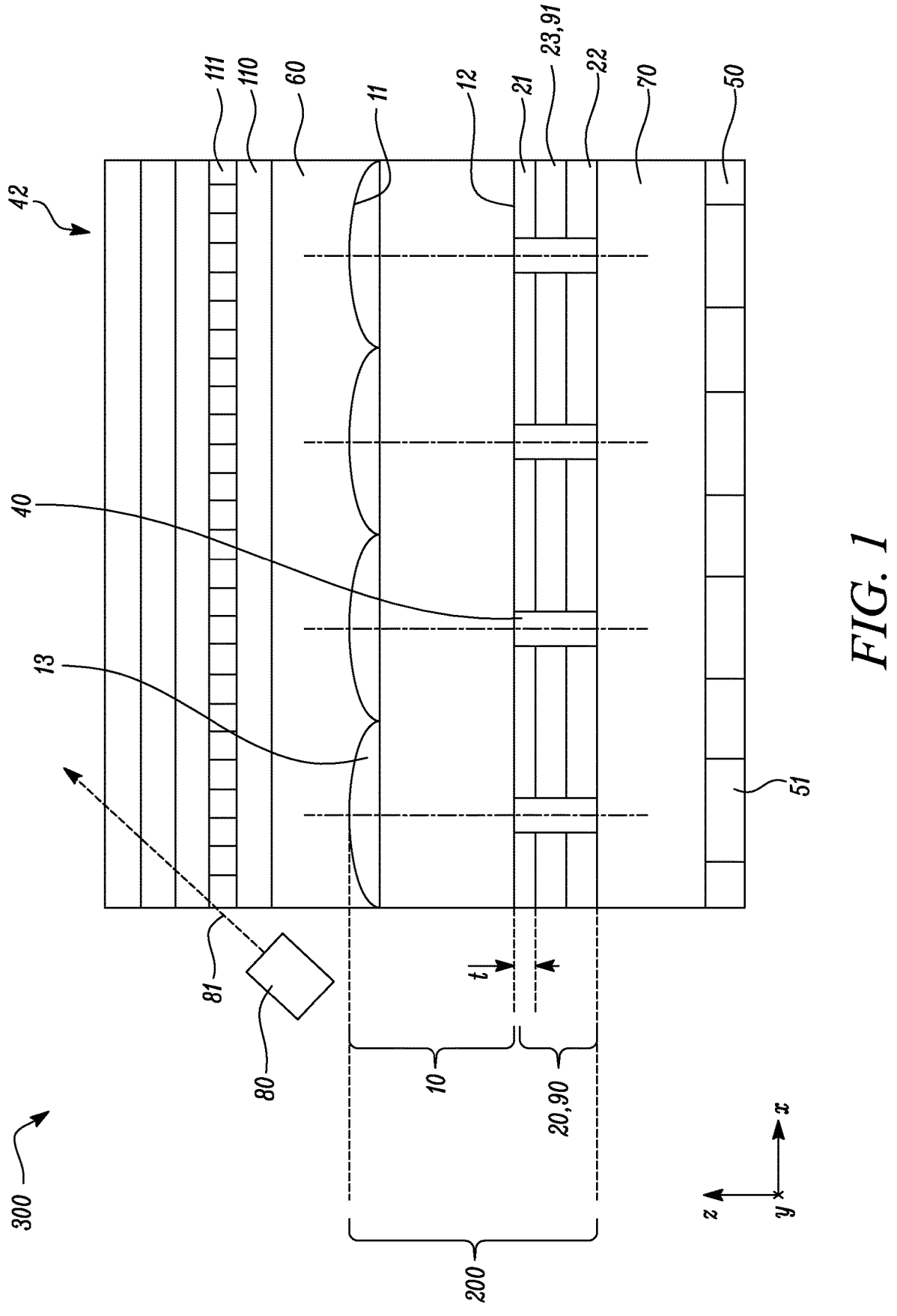
FIG. 1 is a schematic view of an optical system according to one embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

A display with an under-the-display fingerprint sensor may include a display panel, collimation optics, a light blocking layer with holes, and an image sensor. The light blocking layer may have low reflectance and low transmittance in visible range of light in order to improve overall display ambient contrast in a dark state. Conventional displays with the under-the-display fingerprint sensor use black paint as the light blocking layer. However, the black paint may be incompatible with the display fabrication process. Moreover, it may also be difficult to provide holes in the black paint to enable a fingerprint signal to pass through. According to some aspects of the present disclosure, multilayer optically opaque mask layers are provided that address these and other issues with conventional light blocking layers.

The present disclosure relates to an optical system and an optical construction. The optical system includes a display, an optical sensor, and the optical construction. The optical system and the optical construction may be used in electronic devices that include displays, such as computer monitors, televisions, mobile phones, personal digital assistants (PDAs), wearable devices and other portable devices.

The optical construction includes a lens film and a multilayer optically opaque mask layer. The lens film includes an outermost structured first major surface and an opposing outermost substantially planar second major surface. The structured first surface includes a plurality of microlenses arranged along orthogonal first and second directions. The multilayer optically opaque mask layer is disposed on the second major surface of the lens film and includes a first layer, a second layer and a third layer. Each of the first, the second and the third layers has an average thickness less than about 200 nanometers (nm). For a substantially normal incident light with a wavelength in a visible wavelength range, each of the first and the second layers has an optical reflectance of greater than about 5%, and the third layer has an optical transmittance of greater than about 70%. The multilayer optically opaque mask layer has an optical reflectance of less than about 20%. The multilayer optically opaque mask layer defines a plurality of through openings therein extending through at least the first, second and third layers and arranged along the first and second directions. The through openings are aligned to the microlenses in a one-to-one correspondence.

The mask layer may be directly coated on the planar second major surface of the lens film by vacuum coating process, such as electron beam evaporation, thermal evaporation, physical vapor deposition, and chemical vapor deposition or sputtering, thereby simplifying the display fabrication process. By selecting the right combination of materials for different layers and controlling the layer thickness of each layer, the multilayer optically opaque mask layer may achieve low reflectance and low transmittance in visible range of light, and hence may improve overall display ambient contrast in a dark state. Moreover, as the mask layer is thin, the process of drilling the through openings in the mask layer is further simplified and may be carried out by laser ablation.

Referring now to the Figures, FIG. 1 illustrates an optical system 300 including a display 110, and an optical sensor 50 disposed proximate the display 110. The optical system 300 further includes an optical construction 200 for absorbing visible light and transmitting infrared light. The optical construction 200 is disposed between the display 110 and the optical sensor 50.

The optical system 300 defines mutually orthogonal x, y and z-axes. The x and y-axes are in-plane axes of the optical system 300, while the z-axis is a transverse axis disposed along a thickness of the optical system 300. In other words, the x and y-axes are disposed along a plane of the optical system 300, while the z-axis is perpendicular to the plane of the optical system 300. The display 110, the optical construction 200, and the optical sensor 50 of the optical system 300 are disposed adjacent to each other along the z-axis.

In some embodiments, the optical system 300 further includes a first adhesive layer 60. The first adhesive layer 60 bonds the optical construction 200 to the display 110. The first adhesive layer 60 has an index of refraction of less than about 1.3 for at least one wavelength in a visible wavelength range extending from about 400 nm to about 600 nm. In some embodiments, the optical system 300 may further include a second adhesive layer 70. The second adhesive layer 70 bonds the optical construction 200 to the optical sensor 50.

The display 110 includes a plurality of light emitting pixels 111 arrange along first and second directions. The first and second directions are orthogonal to each other. The first direction may be defined along the x-axis and the second direction may be defined along the y-axis. The light emitting pixels 111 may emit light in response to an electric current. The light emitting pixels 111 may include any suitable sub-pixel arrangement, for example, a pentile matrix or an RGB matrix, as per application attributes.

The optical construction 200 includes a lens film 10 and a multilayer optically opaque mask layer 20 or a substantially light absorbing optical cavity system 90. In some embodiments, the optical construction 200 includes the multilayer optically opaque mask layer 20. In some other embodiments, the optical construction 200 includes the optical cavity system 90.

The lens film 10 includes an outermost structured first major surface 11 and an opposing outermost substantially planar second major surface 12. The structured first major surface 11 includes a plurality of microlenses 13 arranged along the orthogonal first and second directions. The plurality of microlenses 13 may be disposed on the optical cavity system 90 and arranged along the first and second directions. Specifically, the lens film 10 including the microlenses 13 is disposed on the optical cavity system 90. The microlenses 13 may have at least one lateral dimension (e.g., diameter) less than 1 millimeter (mm) and any suitable geometry. In some embodiments, the microlenses 13 may include at least one of refractive lenses, diffractive lenses, metalenses (e.g., surface using nanostructures to focus light), Fresnel lenses, spherical lenses, aspherical lenses, symmetric lenses (e.g., rotationally symmetric about an optical axis), asymmetric lenses (e.g., not rotationally symmetric about an optical axis), or combinations thereof.

The mask layer 20 is disposed on the second major surface 12 of the lens film 10, opposite the structured first major surface 11. The mask layer 20 includes a first layer 21, a second layer 22, and a third layer 23 disposed between the first and second layers 21, 22.

The mask layer 20 defines a plurality of through openings 40 therein extending through at least the first, second and third layers 21, 22, 23 and arranged along the first and second directions. The through openings 40 are aligned to the microlenses 13 in a one-to-one correspondence.

The optical cavity system 90 includes opposing first and second reflectors 21, 22 defining an optical cavity 91 therebetween. The first layer 21 may be interchangeably referred to as the first reflector 21. The second layer 22 may be interchangeably referred to as the second reflector 22. The optical cavity 91 has a length less than 200 nm.

Each of the first and second reflectors 21, 22 defines the plurality of through openings 40 therein. The through openings 40 are arranged along the first and second directions and aligned to the microlenses 13 in a one-to-one correspondence.

The through openings 40 may be of any suitable diameter. In some embodiments, each of the through openings 40 may have a diameter from about 1 micron ($\mu$m) to about 5 $\mu$m. In some other embodiments, each of the through openings 40 may have a diameter of about 3 $\mu$m. The through openings 40 may be provided by any suitable process, for example, by laser ablation.

In some embodiments, the optical sensor 50 incudes a plurality of sensor pixels 51 aligned to the microlenses 13 and the through openings 40 in a one-to-one correspondence.

The first layer 21 includes a first metal, and the second layer 22 includes a second metal. In some embodiments, at least one of the first and second layers 21, 22 includes one or more of titanium, chromium, nickel, copper, platinum, cobalt, tungsten, and manganese. In some embodiments, the second layer 22 includes one or more of aluminum, gold and silver. In some embodiments, the first layer 21 includes titanium and the second layer 22 includes aluminum. In some embodiments, the third layer 23 includes an optically transparent dielectric material. In some embodiments, the third layer 23 includes silicon dioxide ($SiO_2$). Selection of the materials of the first, second and third layers 21, 22, 23 may depend on desired optical transmissive and reflective properties of the materials. In some embodiments, the optical construction 200 may trap light by repeated reflections from the first and the second layers 21, 22. The third layer 23 may transmit light to enable such reflections from the first and second layers 21, 22.

In some embodiments, selection of materials of the first and second and third layers 21, 22, 23 may depend upon factors, such as adhesion to a Polyethylene Terephthalate (PET) film, laser ablation feasibility, and material cost.

The first, second and third layers 21, 22, 23 may be directly coated on the second major surface 12 of the lens film 10 by vacuum coating process, such as electron beam evaporation, thermal evaporation, physical vapor deposition, chemical vapor deposition or sputtering, and thereby simplify the fabrication process. Further, by selecting the right combination of materials for the first, second and third layers 21, 22, 23, the mask layer 20 may achieve low reflectance and low transmittance in visible range of light, and hence may improve overall display ambient contrast in a dark state. Moreover, the first, second and third layers 21, 22, 23 may further simplify the process of drilling the through openings 40 in the mask layer 20.

In some embodiments, the first layer 21 has an average thickness t of about 5 nm to about 50 nm, or about 5 nm to about 40 nm, or about 5 nm to about 30 nm, or about 5 nm to about 20 nm. In some embodiments, the second layer 22 has an average thickness t of about 5 nm to about 70 nm, or about 5 nm to about 60 nm, or about 5 nm to about 50 nm, or about 5 nm to about 40 nm. In some embodiments, the third layer 23 has an average thickness t of about 20 nm to about 200 nm, or about 30 nm to about 150 nm, or about 40 nm to about 120 nm, or about 50 nm to about 100 nm.

By optimizing the average thickness t of each of the first, second and third layers 21, 22, 23 for different wavelengths, both low reflectance and low transmittance may be achieved.

Now referring to FIGS. 1 and 2A, the first layer 21 is disposed between the second major surface 12 of the lens film 10 and the third layer 23, such that for substantially normally incident light 30 and for at least one wavelength in a visible wavelength range extending from about 400 nm to about 600 nm, each of the first and second layers 21, 22 has an optical reflectance of greater than about 5%. In some embodiments, for the at least one wavelength in the visible wavelength range, at least one of the first and second layers 21, 22 has an optical reflectance of greater than about 10%, or 15%, or 20%. In some embodiments, for the at least one wavelength in the visible wavelength range, each of the first and second layers 21, 22 has an optical reflectance of greater than about 10%, or 15%. For the at least one wavelength in the visible wavelength range, the third layer 23 has an optical transmittance of greater than about 70%, and the mask layer 20 has an optical reflectance of less than about 20%. In some embodiments, for the at least one wavelength in the visible wavelength range, the mask layer 20 has an optical reflectance of less than about 15%, or 10%. In some embodiments, mask layer 20 may include more than three layers. More than three layers may further reduce the optical reflectance of the mask layer 20.

In some embodiments, the first and second reflectors 21, 22 define the optical cavity 91 such that for substantially normally incident light 30 and a visible wavelength range extending from about 400 nm to about 600 nm, for at least one wavelength in the visible wavelength range, the optical cavity system 90 reflects less than about 20% of the incident light, and transmits less than about 2% of the incident light. Further, for at least one wavelength in the visible wavelength range, the optical construction 200 transmits at least 10% of the incident light 30.

In some embodiments, the optical cavity 91 includes an air gap which has relatively high optical transmittance as compared to the first and second reflectors 21, 22. Repeated reflections of light from the first and second reflectors 21, 22 across the optical cavity 91 may trap light within the optical cavity system 90. Therefore, the optical cavity system 90 may have high optical absorption.

It may be noted that by selecting right combination of materials of the first, second and third layers 21, 22, 23, as well as the optimization of the average thickness t of each of the first, second and third layers 21, 22, 23, low optical transmittance and low optical reflectance of the mask layer 20 may be achieved. For example, a larger average thickness t may be chosen to reduce cross-talk (light from one microlens incident on the through openings 40 aligned with a different microlens), or a smaller average thickness t may be chosen to increase light transmitted through the through openings 40. Similarly, a light absorption of the optical cavity system 90 may be increased by optimizing materials and dimensions of the first and second reflectors 21, 22 and the optical cavity 91.

The optical sensor 50 may be configured to detect a fingerprint and a display device (e.g., a mobile phone) including the display 110 may be configured to determine if the detected fingerprint matches a fingerprint of an authorized user. In some embodiments, the optical system 300 further includes an infrared light source 80 disposed to emit light 81 toward a front side 42 of the display 110. The infrared light source 80 may aid the optical sensor 50 in detecting a fingerprint on the display 110. The infrared light source 80 may be positioned such that the infrared light source 80 emit light 81 towards a suitable direction. Light 81 emitted by the infrared light source 80 may have a wavelength range extending from about 700 nm to about 1 mm.

When a finger is placed on the display 110 of the optical system 300, the finger reflects a light emitted by the display 110 and/or the infrared light source 80. The reflected light travels through the display 110 before reaching the optical construction 200 and the optical sensor 50. The mask layer 20 of the optical construction 200 with the through openings 40 may allow a portion of the reflected light to reach the optical sensor 50 for signal detection. The other portion of the reflected light from the finger, and the light emitted by the display 110 and/or the infrared light source 80 may be absorbed by the mask layer 20.

Now referring to FIG. 2A, the mask layer 20 or the optical cavity system 90 is illustrated. The substantially normally incident light 30 is also illustrated. The mask layer 20 includes the first, second and third layers 21, 22, 23. The incident light 30 may be reflected and transmitted according to one more materials chosen for each of the first, second and third layers 21, 22, 23. The combination of the first, second and third layers 21, 22, 23 may substantially absorb the incident light 30.

The optical cavity system 90 includes the first and second reflectors 21, 22. The incident light 30 may be at least partially reflected by the first and second reflectors 21, 22. The optical cavity system 90 further includes the optical cavity 91 disposed between the first and second reflectors 21, 22. The optical cavity 91 may allow the incident light 30 to circulate in a closed path due to repeated reflections from the first and second reflectors 21, 22. The optical cavity system 90 and the mask layer 20 may trap the incident light 30, and a portion of reflected light from the second layer 22.

FIG. 2B illustrates the first layer 21 of the mask layer 20. In some embodiments, the first layer 21 includes one or more of titanium, chromium, nickel, copper, platinum, cobalt, tungsten, and manganese. In some embodiments, the first layer 21 may include one or more of aluminum, gold and silver. In some embodiments, the first layer 21 has an average thickness of about 5 nm to about 50 nm, or about 5 nm to about 40 nm, or about 5 nm to about 30 nm, or about 5 nm to about 20 nm.

FIG. 2C illustrates the third layer 23 of the mask layer 20. In some embodiments, the third layer 23 includes an optically transparent dielectric material. In some embodiments, the third layer 23 includes $SiO_2$. In some embodiments, the third layer 23 has an average thickness of about 20 nm to about 200 nm, or about 30 nm to about 150 nm, or about 40 nm to about 120 nm, or about 50 nm to about 100 nm.

FIG. 2D illustrates the second layer 22 of the mask layer 20. In some embodiments, the second layer 22 includes one or more of titanium, chromium, nickel, copper, platinum, cobalt, tungsten, and manganese. In some embodiments, the second layer 22 includes one or more of aluminum, gold and silver. In some embodiments, the second layer 22 has an average thickness of about 5 nm to about 70 nm, or about 5 nm to about 60 nm, or about 5 nm to about 50 nm, or about 5 nm to about 40 nm.

Figure 3A:
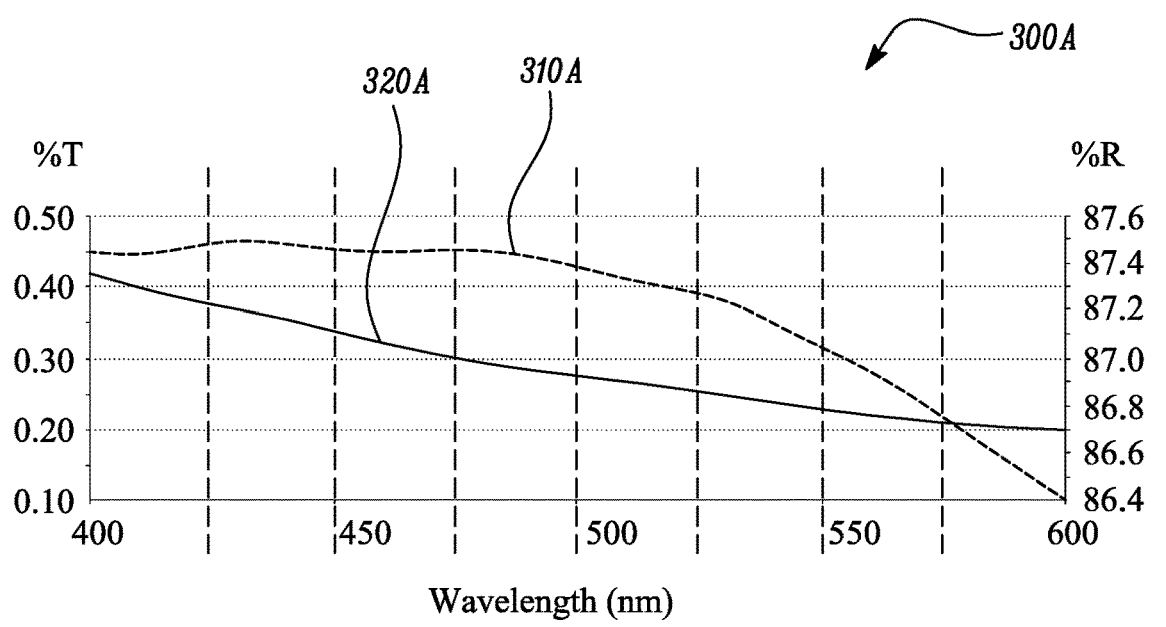
FIG. 3A is a graph illustrating exemplary variations of a transmittance and a reflectance of a light blocking layer with a wavelength of incident light.

Now referring to FIG. 3A, a graph 300A illustrates variations between optical transmittance and optical reflectance with wavelength of an incident light for a PET based collimation optics (e.g., a lens film) coated with a layer of aluminum of about 35 nm thickness. Aluminum was chosen as a light absorbing layer as it may provide ease in drilling micron sized through openings by laser ablation compared to other metals. The transmittance percentage and the reflectance percentage are plotted in the y-axis against the wavelength on the x-axis. Scale of the transmittance percentage is shown on the left y-axis. Scale of the reflectance percentage is shown on the right y-axis. The reflectance percentage is depicted by a curve 310A and the transmittance percentage is depicted by a curve 320A. As depicted by the graph 300A, the transmittance percentage of the incident light is less than about 0.5% for wavelengths from about 400 nm to about 600 nm. However, the reflectance percentage of the incident light is about 87% for wavelengths from about 400 nm to about 600 nm. Therefore, there may be a need to further reduce the reflectance for improving the collimation optics.

Figure 3B:
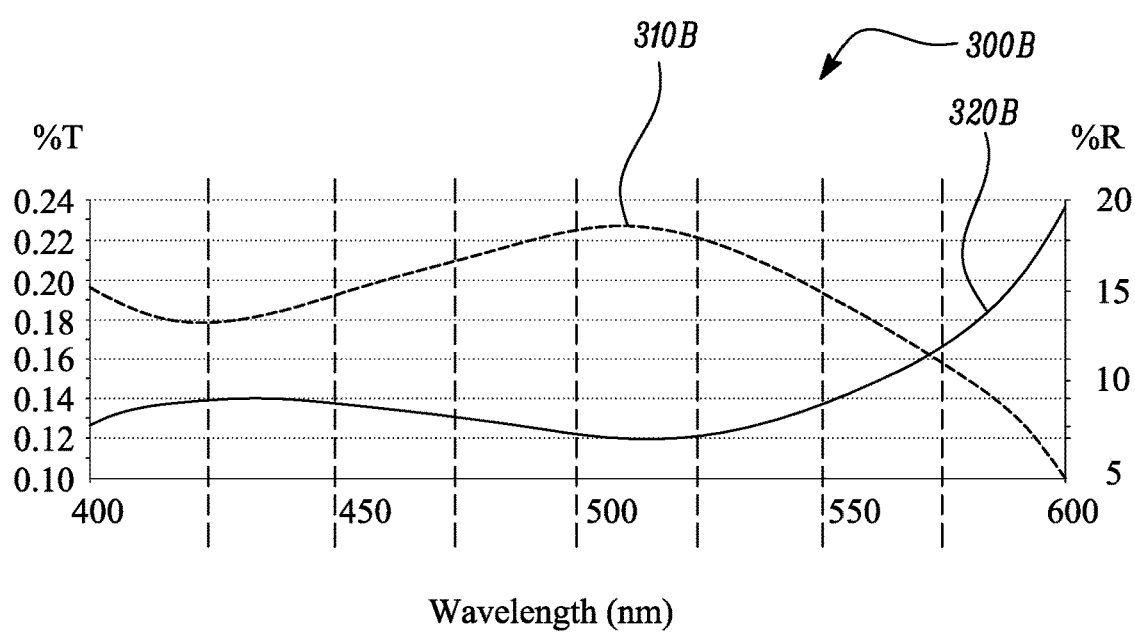
FIG. 3B is a graph illustrating exemplary variations of a transmittance and a reflectance of another light blocking layer with a wavelength of incident light.

Now referring to FIG. 3B, a graph 300B illustrates variations between optical transmittance and optical reflectance with wavelength of an incident light for a PET based collimation optics (e.g., a lens film) coated with a layer of germanium of about 17 nm thickness and a layer of aluminum of about 35 nm thickness. The transmittance percentage and the reflectance percentage are plotted in the y-axis against the wavelength on the x-axis. Scale of the transmittance percentage is shown on the left y-axis. Scale of the reflectance percentage is shown on the right y-axis. The reflectance percentage is depicted by a curve 310B and the transmittance percentage is depicted by a curve 320B. As depicted by the graph 300B, the transmittance percentage of the incident light is less than about 0.24% for wavelengths from about 400 nm to about 600 nm. Further, the reflectance percentage of the incident light is less than about 20% for wavelengths from about 400 nm to about 600 nm. Therefore, the collimation optics coated with the layer of germanium of about 17 nm thickness and the layer of aluminum of about 35 nm thickness has a lower transmittance and a lower reflectance as compared to the collimation optics with coated with a single layer of aluminum of about 35 nm thickness. However, there may be a need to further reduce the transmittance and the reflectance of the collimation optics.

Figure 4:
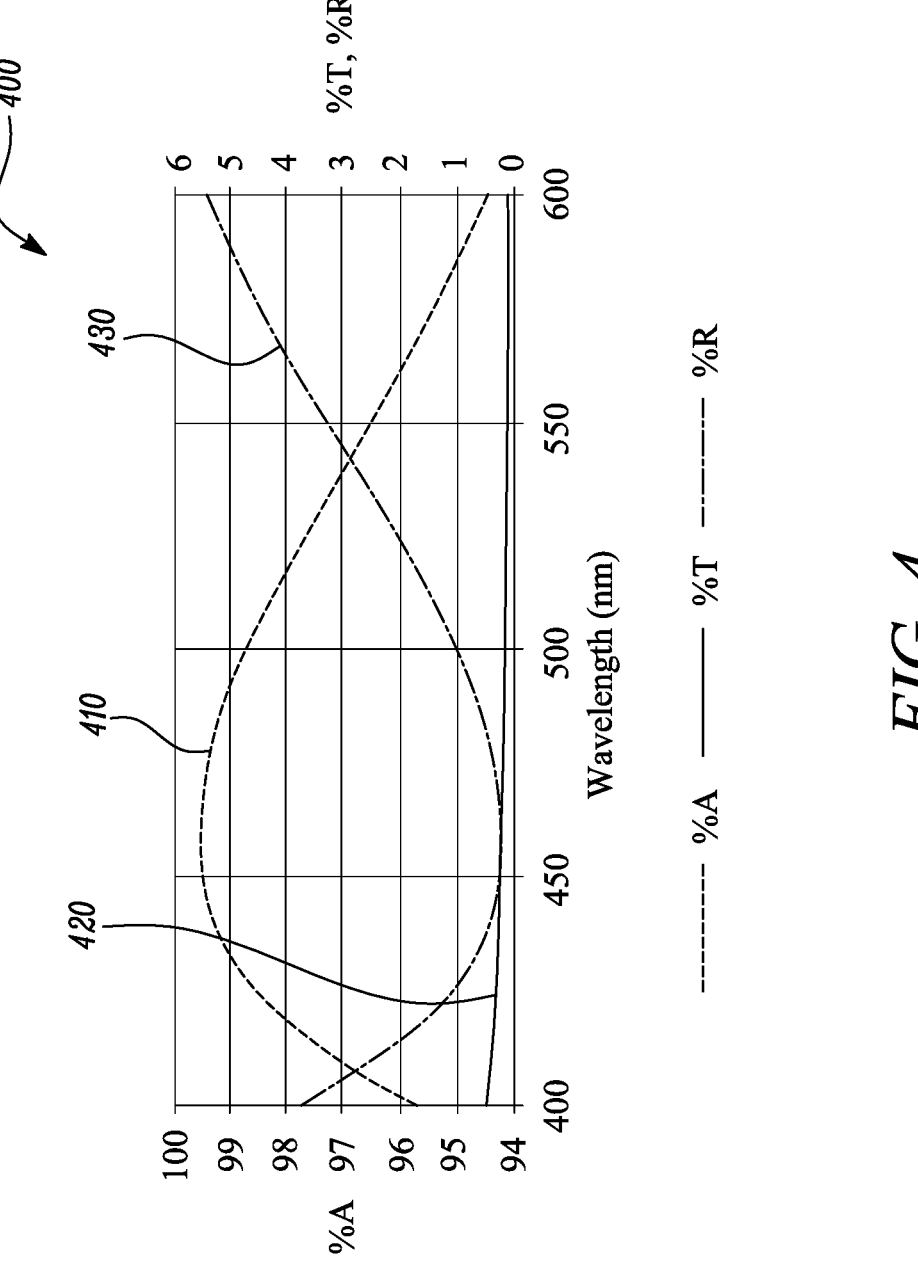
FIG. 4 is a graph illustrating exemplary variations of an absorption, a transmittance and a reflectance of the multilayer optically opaque mask layer with a wavelength of incident light.

Referring to FIGS. 1 and 4, a graph 400 illustrates variations between an optical absorption, an optical transmittance and an optical reflectance of an incident light with wavelength of the optical construction 200 in accordance to an embodiment of the present disclosure. The first layer 21 includes titanium. The average thickness t of the first layer 21 is about 13 nm. The second layer 22 includes aluminum. The average thickness t of the second layer 22 is about 29 nm. The third layer 23 includes $SiO_2$. The average thickness t of the third layer 23 is about 84 nm. The absorption percentage, the transmittance percentage and the reflectance percentage are plotted in the y-axis against the wavelength on the x-axis. Scale of the absorption percentage is shown on the left y-axis. Scale of the transmittance percentage and the reflectance percentage is shown on the right y-axis. The absorption percentage is depicted by a curve 410. The transmittance percentage is depicted by a curve 420. The reflectance percentage is depicted by a curve 430. It may be apparent from the graph 400 that the optical construction 200 exhibits a low reflectance percentage, a low transmittance percentage and a high absorption percentage. The absorption percentage may be equivalent to 100−(Reflectance percentage+Transmittance percentage).

As depicted in the graph 400, the absorption percentage of the incident light is from about 94.5% to about 99.5% for wavelengths from about 400 nm to about 600 nm. The transmittance percentage of the incident light is less than about 0.5% for wavelengths from about 400 nm to about 600 nm. The reflectance percentage of the incident light is less than about 5.5% for wavelengths from about 400 nm to about 600 nm. The optical construction 200 may provide better optical characteristics than other optical configurations discussed above with reference to FIGS. 3A and 3B. Specifically, the optical construction 200 may provide lower transmittance and lower reflectance. The three-layer configuration of the optical construction 200 may therefore provide improved light blocking performance than a single aluminum layer or a two-layer configuration including aluminum and germanium.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. An optical construction comprising:
a lens film comprising an outermost structured first major surface and an opposing outermost substantially planar second major surface, the structured first major surface comprising a plurality of microlenses arranged along orthogonal first and second directions; and
a multilayer optically opaque mask layer disposed on the second major surface of the lens film opposite the structured first major surface and comprising:
a first layer comprising a first metal;
a second layer comprising a second metal; and
a third layer disposed between the first and second layers, each of the first, second and third layers having an average thickness less than about 200 nm, the first layer disposed between the second major surface of the lens film and the third layer, such that for substantially normally incident light and for at least one wavelength in a visible wavelength range extending from about 400 nm to about 600 nm:
each of the first and second layers has an optical reflectance of greater than about 5%;
the third layer has an optical transmittance of greater than about 70%; and
the mask layer has an optical reflectance of less than about 20%; and wherein the mask layer defines a plurality of through openings therein extending through at least the first, second and third layers and arranged along the first and second directions, the through openings aligned to the microlenses in a one-to-one correspondence; and
wherein, for substantially normally incident light over wavelengths from about 400 nm to about 600 nm, the mask layer has an optical reflectance of less than about 10% and an optical transmittance of less than about 1%.

2. The optical construction of claim 1, wherein for the at least one wavelength in the visible wavelength range, each of the first and second layers has an optical reflectance of greater than about 15%.

3. The optical construction of claim 1, wherein for the at least one wavelength in the visible wavelength range, the mask layer has an optical reflectance of less than about 10%.

4. The optical construction of claim 1, wherein the first layer has an average thickness of about 5 nm to about 50 nm, wherein the second layer has an average thickness of about 5 nm to about 70 nm, and wherein the third layer has an average thickness of about 20 nm to about 200 nm.

5. The optical construction of claim 1, wherein the first layer comprises titanium and the second layer comprises aluminum.

6. The optical construction of claim 1, wherein the third layer comprises silicon dioxide.

7. An optical system comprising:
a display comprising a plurality of light emitting pixels arranged along the first and second directions;
an optical sensor disposed proximate the display; and
the optical construction of claim 1 disposed between the display and the optical sensor.

8. The optical system of claim 7, wherein the optical sensor comprises a plurality of sensor pixels aligned to the microlenses and the through openings in a one-to-one correspondence, and wherein the optical system further comprises an infrared light source disposed to emit light toward a front side of the display.

9. The optical system of claim 7, wherein a first adhesive layer bonds the optical construction to the display, the first adhesive layer having an index of refraction of less than about 1.3 for the at least one wavelength.

10. The optical system of claim 9, wherein a second adhesive layer bonds the optical construction to the optical sensor.

* * * * *